(12) United States Patent
Mandell et al.

(10) Patent No.: US 7,267,693 B1
(45) Date of Patent: Sep. 11, 2007

(54) LOCKING RING FOR LINER OF ACETABULAR CUP

(75) Inventors: Steven L. Mandell, Loomis, CA (US); Fredric L. Williams, Riverside, CA (US)

(73) Assignee: Orthopedic Source, Inc., Woodland Hills, CA (US)

( * ) Notice: Subject to any disclaimer, the term of this patent is extended or adjusted under 35 U.S.C. 154(b) by 647 days.

(21) Appl. No.: 10/731,628

(22) Filed: Dec. 8, 2003

(51) Int. Cl.
*A61F 2/32* (2006.01)
(52) U.S. Cl. .................................... 623/22.28
(58) Field of Classification Search ............. 623/16.11, 623/18.11, 22.11, 22.15–22.29
See application file for complete search history.

(56) References Cited

U.S. PATENT DOCUMENTS

| | | | |
|---|---|---|---|
| RE28,895 E | * | 7/1976 | Noiles ...................... 623/22.31 |
| 4,242,775 A | * | 1/1981 | Eickmann ................... 24/16 R |
| 4,380,090 A | | 4/1983 | Ramos |
| 4,408,360 A | | 10/1983 | Keller |
| 4,666,450 A | | 5/1987 | Kenna |
| 4,687,399 A | * | 8/1987 | Petrie ........................ 411/518 |
| 4,695,282 A | | 9/1987 | Forte |
| 4,936,855 A | * | 6/1990 | Sherman .................... 623/22.2 |
| 4,963,154 A | | 10/1990 | Anapliotis |
| 5,314,491 A | | 5/1994 | Thongpreda |
| 5,383,938 A | | 1/1995 | Rohr |
| 5,549,696 A | | 8/1996 | Willi |

* cited by examiner

*Primary Examiner*—Anuradha Ramana
(74) *Attorney, Agent, or Firm*—Heisler & Associates (57) ABSTRACT

An artificial hip joint is provided including a generally hemispherical acetabular cup with a generally hemispherical liner mated within the acetabular cup and with a locking ring to secure the liner within the acetabular cup. The acetabular cup is adapted to be secured within a hip bone. The liner includes a hemispherical inside surface for pivotably supporting a head at an upper end of a femur. The locking ring resides within an annular groove in the acetabular cup and an annular seat in the liner. The locking ring includes a captured end and a free end. The captured end includes a slot which cooperates with a post in the acetabular cup to slidably hold the captured end to the acetabular cup. The locking ring removably attaches the liner to the acetabular cup.

8 Claims, 4 Drawing Sheets

Fig. 18

LOCKING RING FOR LINER OF ACETABULAR CUP

FIELD OF THE INVENTION

The following invention relates to artificial hip joints, and particularly to acetabular cups thereof and the liners within the acetabular cups which rotatably support a head of the artificial hip joint supported by the femur. More particularly, this invention relates to locking rings for securely but removably holding the liner within the acetabular cup.

BACKGROUND OF THE INVENTION

Artificial hip joints have long been used to repair damaged hip joints and to restore maximum function to the hip joint. The hip bone includes an acetabulum in the form of a cup-shaped recess within the hip bone. The acetabulum receives a spherical head joined to an upper end of the femur through a neck. The head is rotatably supported within the acetabulum when the natural hip joint is functioning properly.

In hip joint replacement surgery the acetabulum is appropriately modified to receive an acetabular cup therein. The acetabular cup is typically a rigid hemispherical structure formed of titanium, cobalt chrome and polyethylene or other biocompatible material. The cup has an exterior surface which is roughened such as with a porous coating or grit blasted to encourage bone interdigitation. A top bore is provided passing through an uppermost portion of the acetabular cup. This top bore is utilized in properly aligning the acetabular cup and to optionally receive a screw plug to prevent fluid migration therethrough. Side holes are typically provided passing through the acetabular cup should additional bone screws or other fasteners be needed to secure the acetabular cup to the hip bone.

The interior surface of the acetabular cup has this top bore and side holes passing therethrough, and so is not optimally formed to bear loads associated with the head of the artificial hip joint directly there against. Hence, a liner is provided which mates within the acetabular cup with an outside surface of the liner abutting the interior surface of the acetabular cup. The inside surface of the liner is hemispherical and provides the bearing surface to support the ball of an artificial hip joint which is secured to an upper end of the femur and rotatably supports the head of the femur therein. The liner is secured to the acetabular cup through a locking ring which fits within both a groove in the interior surface of the acetabular cup and within a seat in the outside surface of the liner.

Locking rings are known in the art for securing a liner within an acetabular cup. For instance, the patent to Rohr (U.S. Pat. No. 5,383,938), Thongpreda (U.S. Pat. No. 5,314,491) and Ramos (U.S. Pat. No. 4,380,090) each teach generally circular locking rings with a break therein and with two free ends. The free ends can be drawn together or pushed apart to insert such locking rings into associated grooves and seats within the acetabular cup and liner to secure the liner within the acetabular cup. Such locking rings, while generally effective, can be difficult to insert, and typically once the liner has been secured within the acetabular cup, such locking rings are difficult, if not impossible, to remove, should it be desired by a surgeon to remove the liner after it has been placed within the acetabular cup with the locking ring. Accordingly, a need exists for a locking ring which is easy to insert to secure a liner within an acetabular cup and which can be easily removed to allow the liner to be removed from the acetabular cup if desired, particularly by a surgeon during a surgical procedure with the minimum potential complication.

Additionally, one particular problem with prior art acetabular cups and liners of artificial hip joints is that the top bore, unless plugged with an optional screw plug, provides a region for the passage of fluids from adjacent the hip bone through the acetabular cup and into the artificial hip joint, or for the passage of wear debris from within the artificial hip joint into contact with the hip bone. Wear debris can discourage bone growth into the exterior surface of the acetabular cup, increasing the possibility of failure of the artificial hip joint. Fluid migrating through the top bore into the artificial hip joint can decrease the operational effectiveness of the artificial hip joint. Hence, it is desirable that this top bore be sealed.

Some prior art acetabular cups and liners are known to include posts or other structures passing into the top bore of the acetabular cup. However, such posts have not been taught to seal such a passage in the acetabular cup, but rather have been provided to secure the liner within the acetabular cup or to provide for alignment of the liner within the acetabular cup. Representative prior art devices are disclosed by Kenna (U.S. Pat. No. 4,666,450), Willi (U.S. Pat. No. 5,549,696) and Forte (U.S. Pat. No. 4,695,282). Accordingly, a need exists for a liner which, in addition to providing the proper bearing surface for the ball of the femur, additionally seals a top bore passing through the acetabular cup.

SUMMARY OF THE INVENTION

With this invention, a locking ring is provided particularly for use in securing two concentric structures together, such as an acetabular cup and a liner of an artificial hip joint. The locking ring is configured to be used with a first structure which includes an annular groove extending inwardly from a rim of the first structure and to fit within an annular seat facing outwardly from a brim of a second structure which nests within the first structure.

The locking ring has a break therein separating a captured end from a free end. The captured end is captured in some fashion to the first structure, such as the acetabular cup. This capturing means is preferably slidable, such as in the form of a post in the first structure residing within a slot in the captured end of the locking ring. The free end of the locking ring is adapted to be grasped so that the free end can be forced away from the captured end to expand a diameter of the locking ring. Such expansion moves the locking ring out of the seat and facilitates removal of the second structure, such as the liner, from the first structure, such as the acetabular cup. The locking ring can also accommodate snapping of the liner or other second structure easily into alignment mating with the first structure when the locking ring residing within the groove of the first structure snaps into the seat of the second structure.

OBJECTS OF THE INVENTION

Accordingly, a primary object of the present invention is to provide a locking ring for an artificial hip joint to secure a liner within an acetabular cup with the locking ring being easy to insert to hold the liner within the acetabular cup and easy to remove or expand to allow the liner to be removed from the acetabular cup or to be easily released and rotated to a desired position and reattached with the locking ring.

Another object of the present invention is to provide a locking ring which can be quickly and easily inserted into a groove in the acetabular cup and a seat within the liner to hold the liner within the acetabular cup.

Another object of the present invention is to provide a locking ring which can be easily removed from a groove within the acetabular cup and a seat within the liner, should the liner need to be removed from the acetabular cup.

Another object of the present invention is to provide an artificial hip joint which can be safely, quickly and easily implanted into a patient.

Other further objects of the present invention will become apparent from a careful reading of the included drawing figures, the claims and detailed description of the invention.

BRIEF DESCRIPTION OF THE DRAWINGS

Note that FIGS. 14-18 show structures inverted relative to their appearance in FIGS. 1 and 2.

DESCRIPTION OF THE PREFERRED EMBODIMENT

Referring to the drawings, wherein like reference numerals represent like parts throughout the various drawing figures, reference numeral 10 is directed to an acetabular cup (FIG. 1) adapted to receive a liner 30 therein for a portion of an artificial hip joint assembly 2 coupled to a hip bone. A locking ring 60 is provided to secure the liner 30 within the acetabular cup 10. With this artificial hip joint assembly 2 (FIGS. 1 and 2) a top bore 20 within the acetabular cup 10 is sealed by a top cone 40 of the liner 30 when the liner 30 is secured within the acetabular cup 10 by the locking ring 60. The locking ring 60 is easily positioned to hold the liner 30 within the acetabular cup 10 and easily enlarged to allow removal of the liner 30 from the acetabular cup 10.

Figure 1:
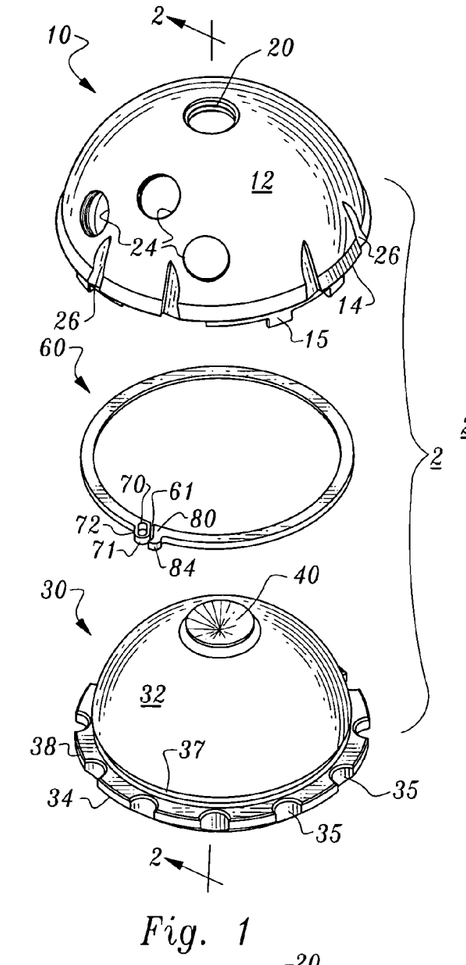
FIG. 1 is a perspective exploded parts view of the artificial hip joint assembly including the acetabular cup, liner and locking ring of this invention, shown partially from above.
Figure 2:
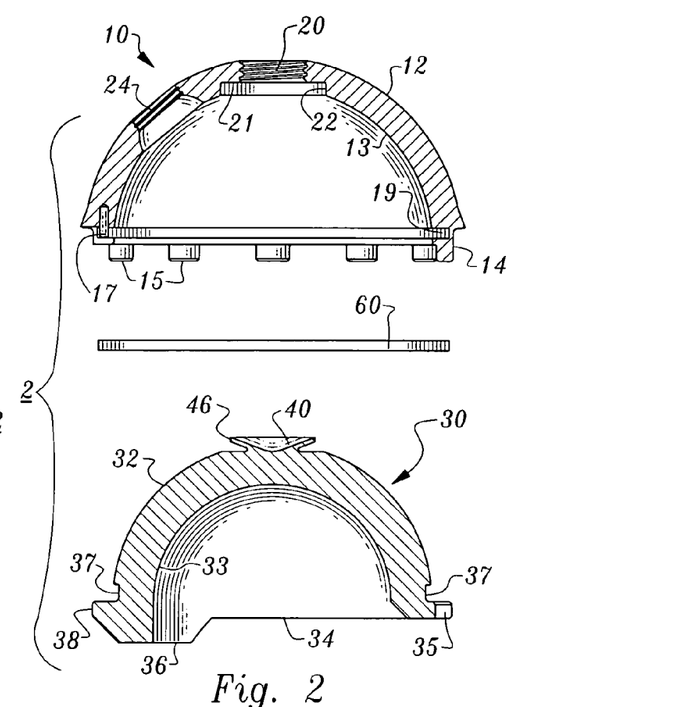
FIG. 2 is a full sectional exploded parts view of that which is shown in FIG. 1 except that the locking ring is not shown in section.

In essence, and with particular reference to FIGS. 1 and 2, basic details of the artificial hip joint assembly 2 are described. The acetabular cup 10 is a generally hemispherical rigid structure having an exterior surface 12 adapted to be secured to a hip bone. An interior surface 13 of the acetabular cup 10 receives the liner 30 therein. A top bore 20 passes from the interior surface 13 through the exterior surface 12 of the acetabular cup 10. The top bore 20 assists in alignment of the acetabular cup 10 during implantation. The liner 30 is configured to seal off the top bore 20 to prevent the passage of fluid or wear debris through the top bore 20.

The liner 30 is a second generally hemispherical rigid structure that nests within the acetabular cup 10. The liner 30 includes a top cone 40 which is sized to surround the top bore 20 and seal the top bore 20. The top cone 40 provides a preferred form of the forming seal for sealing of the top bore 20.

The locking ring 60 is a generally circular ring with a break 61 therein separating a captured end 70 from a free end 80. An annular groove 19 in the acetabular cup 10 and an annular seat 37 in the liner 30 face each other within a common plane and are sized to receive the locking ring 60 therein when the liner 30 is mated entirely within the acetabular cup 10. The captured end 70 is secured to the acetabular cup 10 through a post 17 in the acetabular cup 10 passing through a slot 72 at the captured end 70 of the locking ring 60. The free end 80 includes a finger 84 which can be grasped to move the free end 80 away from the captured end 70 to allow for easy removal of the liner 30 out of the acetabular cup 10. The slot 72 allows the captured end 70 to slide somewhat upon the post 17 of the acetabular cup 10 to facilitate further the removal of the liner 30 from the acetabular cup 10.

More specifically, and with particular reference to FIGS. 1-7, particular details of the acetabular cup 10 are described. The acetabular cup 10 can be any form of acetabular cup which requires a liner therein. The features of this invention are most particularly useful with acetabular cups 10 which have liners 30 secured therein through a locking ring 60 positioned within the annular groove 19 of the acetabular cup 10 and to acetabular cups 10 which include a top bore 20 passing between the interior surface 13 and the exterior surface 12.

Most preferably, the acetabular cup 10 is a hollow hemispherical rigid construct, typically formed from a biocompatible metal such as stainless steel or titanium. The exterior surface 12 is typically roughened to encourage bone growth from the hip bone into the exterior surface 12, such that the exterior surface 12 is securely bonded to the hip bone when implanted. The interior surface 13 is typically smooth and hemispherical and oriented to provide a thickness of the acetabular cup 10 which is substantially constant between the interior surface 13 and the exterior surface 12. A rim 14 defines a lowermost portion of the acetabular cup 10 which joins the interior surface 13 to the exterior surface 12. The rim 14 most preferably includes teeth 15 extending downward therefrom. The teeth 15 cooperate with gaps 35 in the liner 30 to assist in securing the liner 30 within the acetabular cup 10 as discussed in detail below.

The rim 14 preferably includes a space 16 at one location there along. This space 16 has a post 17 extending parallel with a central axis of the acetabular cup 10. This space 16 is preferably aligned with the annular groove 19 circumscribing the interior surface 13 of the acetabular cup 10 near the rim 14. A surface 18 of the space 16 is generally planar and parallel with the annular groove 19 and perpendicular with the central axis of the acetabular cup 10. The post 17 extends perpendicularly from the surface 18. The post 17 is preferably rigid and formed by press fitting a pin into a blind bore extending perpendicularly into the surface 18. The post 17 assists in holding the captured end 70 of the locking ring 60 adjacent thereto, as discussed in detail below.

A top bore 20 preferably passes entirely into the acetabular cup 10 from the interior surface 13 to the exterior surface 12. This top bore 20 is preferably threaded and includes a planar shelf 21 where the top bore 20 transitions with the interior surface 13. A perimeter 22 extends perpendicularly from the planar shelf 21 to join the shelf 21 with curving portions of the interior surface 13. The shelf 21 preferably is substantially circular, but preferably with at least two facets thereon. Such a shelf can accommodate both circular and irregularly shaped structures therein.

Preferably at least three side holes 24 pass from the interior surface 13 through to the exterior surface 12 and are threaded in a manner similar to the top bore 20. The side holes 24 provide locations where additional bone screws or other attachment devices can be utilized if necessary to securely hold the acetabular cup 10 to the hip bone.

Most typically, the side holes 24 are filled with plugs and are not needed. If one of the side holes 24 (or more) are needed, the plug is removed from the side hole 24 and an appropriate bone screw or other attachment device is utilized within the side hole 24 vacated by the plug that has been removed. The top bore 20 is provided for proper positioning of the acetabular cup 10. Specifically, an insertion tool can engage the cup 10 by threading into the top bore 20. Once the cup 10 is inserted the tool is removed. The bore 20 can then be used to measure and observe the position of the cup 10. Typically, the top bore 20 remains open after the implantation of the acetabular cup 10 is complete. To make sure that fluids or wear debris do not pass through the top bore 20, a plug can be threaded into the top bore 20 or some other post can be placed within the top bore 20. However, if a plug is utilized, an additional step is required during the acetabular cup 10 implantation process. Where a post is provided, less than a complete seal of the top bore 20 is provided. With this invention the top cone 40 on the liner 30 seals the top bore 20 completely and does not require an extra step to provide such a seal for the top bore 20.

Notches 26 are typically formed extending within the exterior surface 12 in the rim 14, extending partially toward an uppermost portion of the exterior surface 12. These notches 26 assist in securing the acetabular cup 10 to the hip bone and in resisting rotation of the acetabular cup 10 relative to the hip bone. The notches 26 and other particular features of the acetabular cup 10 can be varied depending upon the particular artificial hip joint involved to maximize effectiveness of the overall assembly 2.

With particular reference to FIGS. 1-4 and 8-13, details of the liner 30 are described. the liner 30 can be any form of liner 30 adapted to mate within an acetabular cup 10. The preferred form of liner 30 according to this invention is provided with the top cone 40 to seal the top bore 20 of the acetabular cup 10 and with an annular seat 37 in the outside surface 32 of the liner 30 to secure the liner 30 to the acetabular cup 10 with the locking ring 60.

The liner 30 is a generally hemispherical rigid construct typically formed of a relatively soft and resilient, but high wear material, such as delron, nylon or other polymeric hydrocarbon material which exhibits biocompatibility and suitable performance for supporting the head of an artificial hip joint extending from an upper end of a femur. The liner 30 includes an outside surface 32 sized and shaped to mate closely with the interior surface 13 of the acetabular cup 10. An inside surface 33 of the liner 30 preferably is a smooth hemisphere which provides a bearing surface for rotational support of the head of the femur of the artificial hip joint.

A brim 34 defines a lowermost portion of the liner 30 which defines a transition between the outside surface 32 and the inside surface 33. The brim 34 includes gaps 35 therein which are positioned and shaped to receive the teeth 15 of the acetabular cup 10 therein. Thus, when the liner 30 is located entirely within the acetabular cup 10, the teeth 15 and gaps 35 act together to prevent rotation of the liner 30 relative to the acetabular cup 10. The brim 34 of the liner 30 includes an extension 36 on slightly less than half of the brim 34. The extension 36 extends downward an additional amount. The extension 36 is preferable to provide additional bearing surface on one side of the liner 30 to provide maximum support for the head of the femur therein.

A seat 37 extends annularly into the outside surface 32 of the liner 30 directly above the brim 34 of the liner 30. The seat 37 is positioned to be coplanar with the annular groove 19 of the acetabular cup 10 when the liner 30 is mated entirely within the acetabular cup 10. The liner 30 includes a lip 38 which extends radially from the brim 34 and includes the gaps 35 therein. The lip 38 is configured to abut the rim 14 of the acetabular cup 10 when the liner 30 is mated entirely within the acetabular cup 10.

Figure 13:
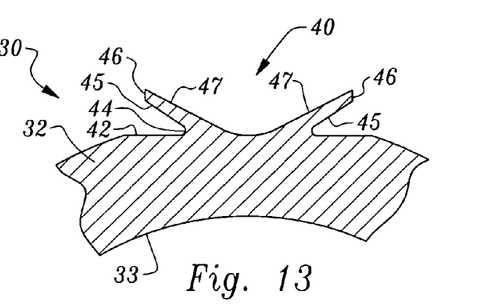
FIG. 13 is a sectional view of an uppermost portion of the liner according to this invention, particularly revealing details of the top cone of the liner of this invention.

A top cone 40 provides the preferred form of deforming seal or other sealing means extending from the outside surface 32 of the liner 30 at an uppermost portion of the liner 30 and at a centerline of the liner 30. The top cone 40 preferably is formed with the liner 30 and of the same material which forms the liner 30. Alternatively, the top cone 40 could be a separate piece from the liner 30, formed of either a separate material or the same material as the liner 30. If the top cone 40 is provided as a separate structure from the liner 30, the top cone 40 can rest within a recess in the outside surface 32 of the liner 30 such that the top cone 40 would remain within the liner 30, or can otherwise be provided with alignment structures to provide the top cone 40 precisely where needed to seal the top bore 20 of the acetabular cup 10.

The top cone 40 according to the preferred embodiment of this invention extends upward from a center of a flat 42 in the outside surface 32 of the liner 30. A neck 44 extends up from the flat 42 and defines a curve which transitions the flat 42 from a planar horizontal orientation up into the outer conical surface 45 of the top cone 40. The outer conical surface 45 extends upwardly and outwardly to an edge 46. The edge 46 is preferably generally circular and defines a portion of the top cone 40 which abuts the acetabular cup 10, and particularly the shelf 21 surrounding the top bore 20 of the acetabular cup 10. If no shelf 21 is provided surrounding the top bore 20, the edge 46 can still abut portions of the acetabular cup 10 surrounding the top bore 20.

Figure 3:
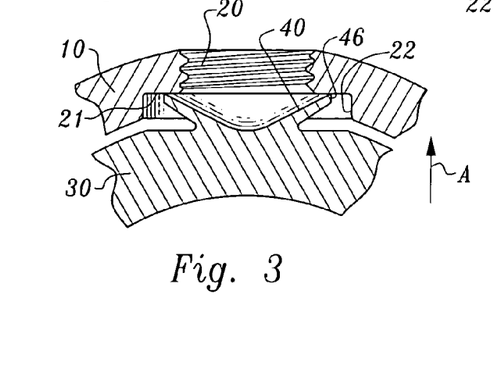
FIG. 3 is a sectional view of a portion of the liner and a portion of the acetabular cup shown adjacent each other just before being fully mated together.
Figure 4:
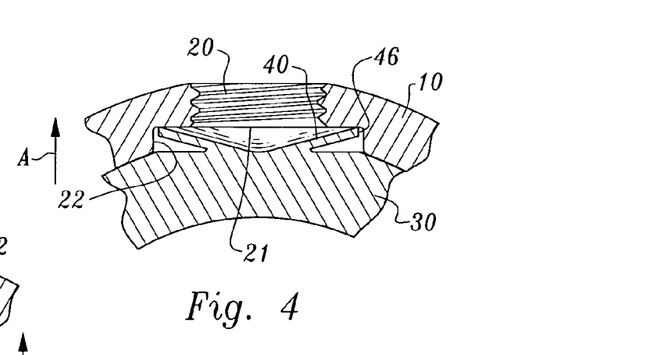
FIG. 4 is a full sectional view similar to that which is shown in FIG. 3 but after the liner has been fully mated within the acetabular cup to seal a top bore of the acetabular cup with the top cone of the liner.
Figures 5, 6, 7:
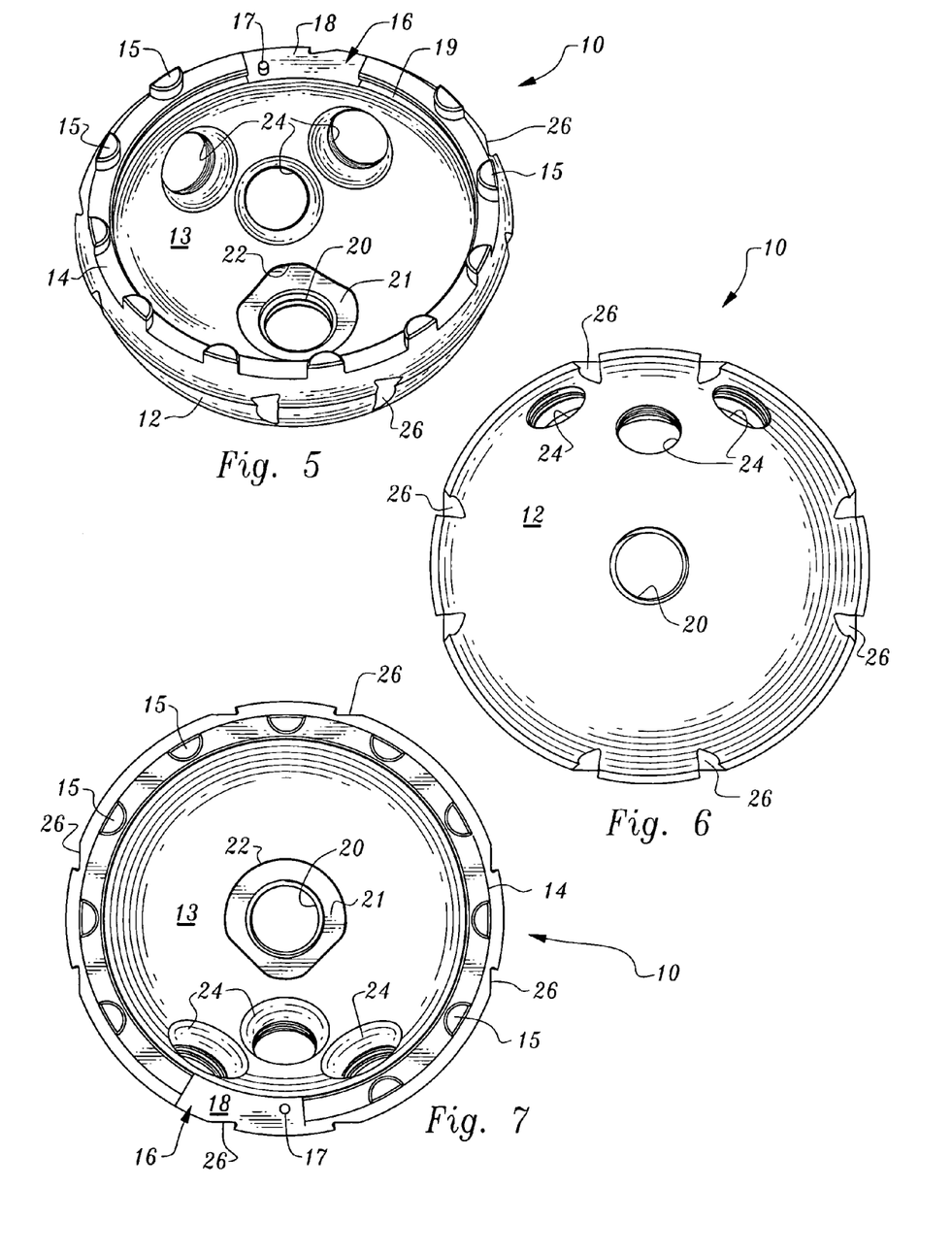
FIG. 5 is a perspective view of the acetabular cup according to this invention, shown partially from below.
FIG. 6 is a top plan view of the acetabular cup according to this invention.
FIG. 7 is a bottom plan view of the acetabular cup according to this invention.
Figure 8:
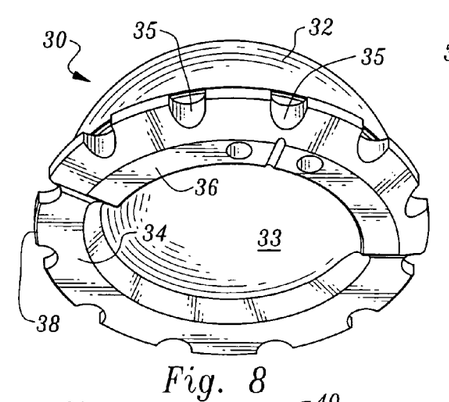
FIG. 8 is a perspective view of the liner according to this invention, shown partially from below.
Figure 9:
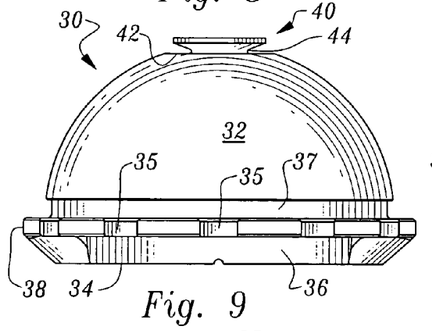
FIG. 9 is a front elevation view of the liner according to this invention.
Figure 10:
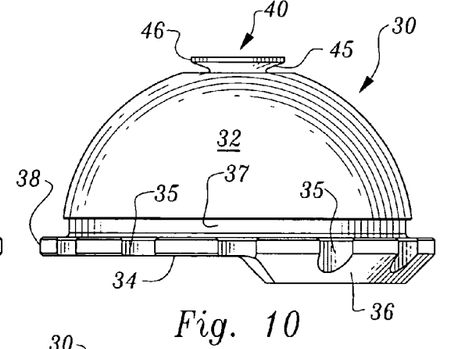
FIG. 10 is a side elevation view of the liner according to this invention.
Figure 11:
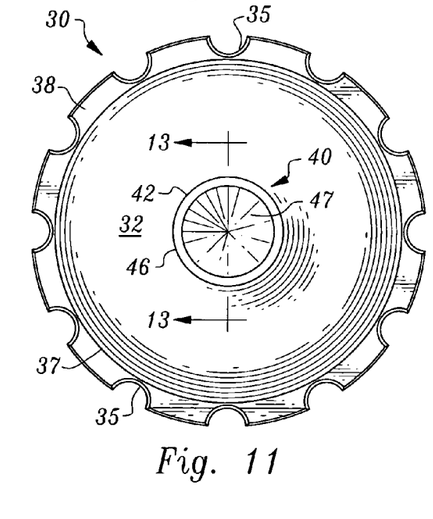
FIG. 11 is a top plan view of the liner according to this invention.
Figure 12:
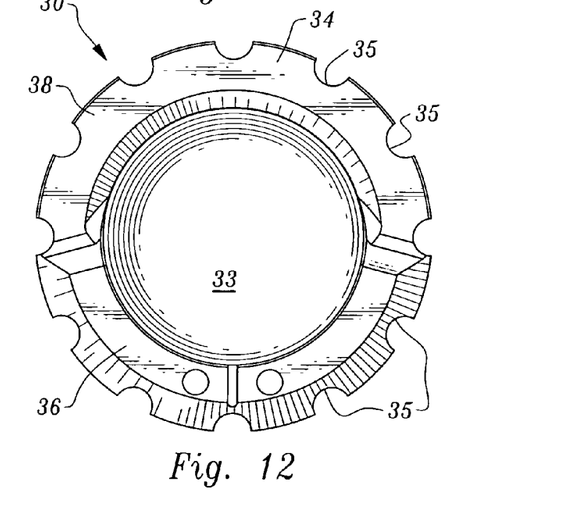
FIG. 12 is a bottom plan view of the liner according to this invention.

An inner conical surface 47 extends downwardly and inwardly from the edge 46 to a center line of the liner 30. The top cone 40 is thus a somewhat thin walled hollow conical structure extending upward from the outside surface 32 of the liner 30. Because the top cone 40 is relatively thin walled, it can deflect somewhat (FIGS. 3 and 4) when the liner 30 is fully mated within the acetabular cup 10 (FIG. 4), such as when the liner 30 is moved into contact with the acetabular cup 10 along arrow A (FIGS. 3 and 4). Other forms of deforming seals could similarly be utilized which deform when coming into contact with the acetabular cup 10 to provide a seal surrounding the top bore 20 of the acetabular cup 10.

With particular reference to FIGS. 1, 2 and 14-18, details of the locking ring 60 of the preferred embodiment of this invention are described. While the preferred locking ring 60 is shown herein, any form of locking ring 60 can be utilized to some beneficial effect, with one captured end and one free end preferably provided according to this invention. The most preferable locking ring 60 further includes the slot 72 within the captured end 70 and utilization of the post 17 of the acetabular cup 10 within the slot 72 to maximize use in placing the locking ring 60 into the annular groove 19 and annular seat 37 and in removing the liner 30 from the acetabular cup 10.

The locking ring 60 is preferably a substantially rigid annular construct formed of a resilient material, such as a spring steel or a biocompatible material with sufficient strength to allow it to be expanded somewhat without exceeding an elastic limit for the material forming the ring 60. The ring 60 includes a break 61 which separates the captured end 70 from the free end 80.

Figures 14, 15, 16:
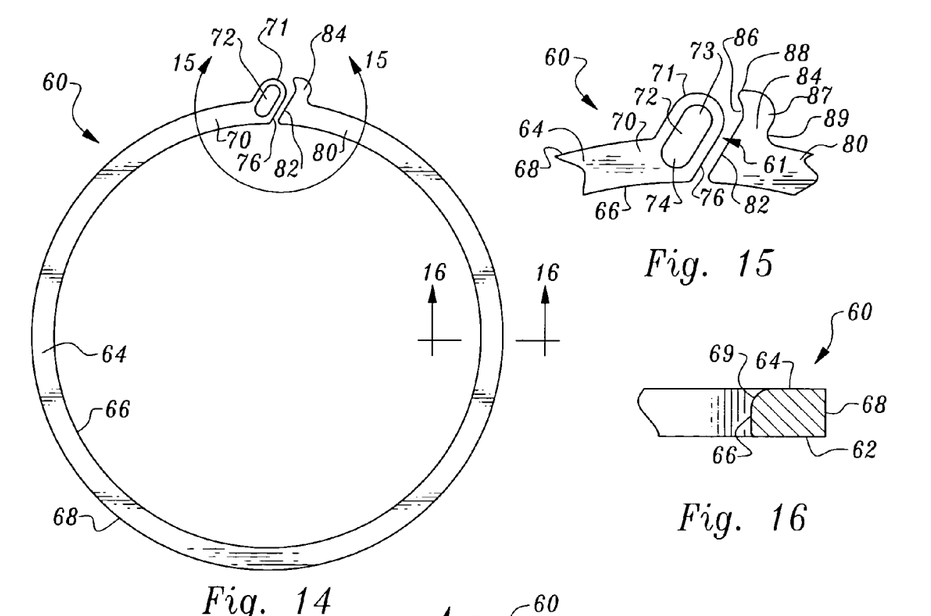
FIG. 14 is a bottom plan view of the locking ring according to this invention.
FIG. 15 is a detail of a portion of that which is shown in FIG. 14.
FIG. 16 is a sectional view of a portion of that which is shown in FIG. 14, with the section taken along line 16-16 of FIG. 14.

The locking ring 60 preferably has a substantially constant square cross-section with a top side 62 parallel with and spaced from a bottom side 64. A thickness of the locking ring 60 is defined by a distance between the top side 62 and the bottom side 64. An inner side 66 and outer side 68 maintain a constant spacing therebetween defining a width of the locking ring 60.

The thickness of the locking ring 60 is similar to but slightly less than a thickness of the annular groove 19 of the acetabular cup 10 and the annular seat 37 of the liner 30. The width of the locking ring 60 is preferably somewhat less than a distance between the innermost surface of the annular groove 19 of the acetabular cup 10 and the innermost surface of the annular seat 37 of the liner 30, such that the locking ring 60 can reside in both the annular groove 19 and the annular seat 37 simultaneously, and still have sufficient play so that when the locking ring 60 is expanded it can release out of the annular seat 37 of the liner 30 so that the liner 30 can be removed from the acetabular cup 10. Preferably, a beveled edge 69 is provided between the bottom side 64 and the inner side 66 to encourage expansion of the locking ring 60 when the liner 30 is pressed up into the acetabular cup 10 (along arrow C of FIG. 17).

The captured end 70 is preferably provided with some form of a means to hold the captured end 70 in a slidable fashion to the acetabular cup 10. This slidable holding means is preferably in the form of a slot 72 extending between an outer end 73 and an inner end 74. The outer end 73 extends up into a nob 71 of the captured end 70 which extends beyond the outer side 68 of the locking ring 60. The slot 72 preferably has a width similar to that of the post 17 and a length between the outer end 73 and inner end 74 which allows the slot 72 to slide along the post 17 somewhat (along arrow F of FIG. 17).

Figure 17:
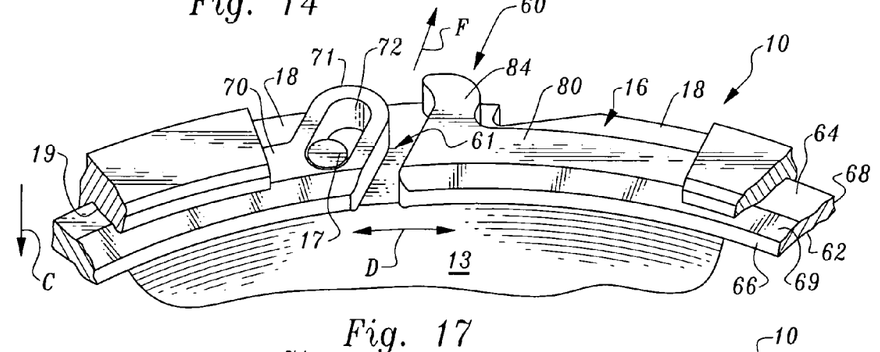
FIG. 17 is a perspective view of the locking ring within a groove in the acetabular cup shown partially from below and with the locking ring having been expanded and ready to return to an original undeformed diameter to secure a liner within the acetabular cup.
Figure 18:
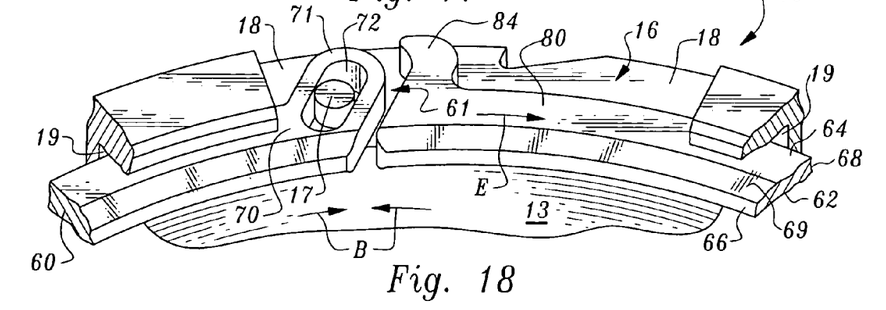
FIG. 18 is a perspective view similar to that which is shown in FIG. 17 but with the locking ring having returned to its original undeformed shape with a narrower break therein and in a position where it can secure a liner within the acetabular cup.

The tip of the captured end 70 is preferably angled along with the slot 72 so that the outer end 73 of the slot 72 extends further circumferentially than the inner end 74 (in a clockwise direction in FIGS. 17 and 18). This angling of the slot 72 causes the captured end 70 of the locking ring 60 to extend radially outwardly (along arrow F) when a circumferential force is applied to the free end 80 of the locking ring 60 (along arrow E of FIG. 18), causing the locking ring 60 to rotate circumferentially. In this way, the locking ring 60 is encouraged to move out of the seat 37 of the liner 30 to allow the liner 30 to be removed.

The free end 80 of the locking ring 60 includes an end wall 82 generally parallel with the angled tip 76 of the captured end 70 and spaced from the captured end 70 by a width of the break 61. A finger 84 extends radially from the outer side 68 of the locking ring 60 and defines a region which can be easily grasped by a surgeon, such as with forceps or fingers of the surgeon, when the liner 30 is to be removed from the acetabular cup 10 or when the liner 30 is to be rotated to a more desirable orientation.

The end wall 82 includes a trough 86 near a portion of the finger 84 directly below a head 87 of the finger 84 and below a nose 88 in a head 87 of the finger 84. A curve 89 defines a side of the finger 84 opposite the end wall 82. The trough 86 defines a saddle where a single probe can be easily placed to provide a circumferential force (along arrow E of FIG. 18) to rotate the locking ring 60 and to remove the locking ring 60 out of the seat 37 of the liner 30.

The curve 89 preferably curves back slightly toward the end wall 82 to provide a region where a probe or other device can be placed to ensure that the free end 80 has returned fully back toward the captured end 70 when the liner 30 has been replaced within the acetabular cup 10. This curve 89 can also be utilized along with the trough 86 with forceps or other dual pronged grasping tools so that the finger 84 can be securely grasped and manipulated when desired. The trough 86, curve 89 and head 87 provide forms of a means to grasp the finger 84 at the free end 80 of the locking ring 60. The curve 89 can cooperate with the trough 86 to provide another form of means to grasp the finger 84 of the free end 80.

In use and operation, and with particular reference to FIGS. 3 and 4, details of the use and operation of the top cone 60 to seal the top bore 20 of the acetabular cup 10 are described. After the acetabular cup 10 has been secured in the desired position relative to the hip bone, the liner 30 is located within the acetabular cup 10. The outside surface 32 (FIG. 2) of the liner 30 is brought close to the interior surface 13 (FIG. 2) of the acetabular cup 10. The edge 46 of the top cone 40 then comes into contact with the interior surface 13 of the acetabular cup 10, preferably against the shelf 21 surrounding the top bore 20 (FIG. 3).

With further translation of the liner 30 up into the acetabular cup 10 (along arrow A of FIGS. 3 and 4), the top cone 40 is deflected somewhat with the edge 46 of the top cone 40 being pivoted toward the outside surface 32 of the liner 30 and with the edge 46 providing a preferred form of a deforming seal or other sealing means surrounding the top bore 20 of the acetabular cup 10. The liner 30 is held in position adjacent the acetabular cup 10 with the top cone 40 surrounding the top bore 20 by the locking ring 60 (FIG. 1) having snapped into position within the annular groove 19 (FIG. 2) of the acetabular cup 10 and the annular seat 37 of the liner 30.

With particular reference to FIGS. 14-18, details of the use and operation of the locking ring 60 to secure the liner 30 within the acetabular cup 10 are described. Initially, the locking ring 60 is placed within the annular groove 19 of the acetabular cup 10 without the liner 30 within the acetabular cup 10. To position the locking ring 60 within the annular groove 19, the slot 72 of the captured end 70 is placed over the post 17 on the acetabular cup 10. The finger 84 of the free end 80 is then grasped and forced toward the captured end 70 to decrease a width of the break 61. This closure of the break 61 (arrow B of FIG. 18) decreases a diameter of the locking ring 60.

Additionally, by grasping only the free end 80 and moving it towards the captured end 70, the post 17 draws the slot 72 of the captured end 70 inward relative to the acetabular cup 10 and away from the annular groove 19. This allows the locking ring 60 to achieve a diameter sufficiently small so that it can be oriented in the same plane as the annular groove 19 and directly radially inward of the annular groove 19. The finger 84 of the free end 80 can then be relaxed away from the captured end 70 so that the locking ring 60 extends radially outward into the annular groove 19. When the locking ring 60 is at rest, the post 17 is typically at a midpoint between the outer end 72 and inner end 74 of the slot 72. The locking ring 60 is within the annular groove 19 but extends slightly out of the annular groove 19. The acetabular cup 10 and locking ring 60 are now in proper position to receive the liner 30.

The liner 30 is translated upward into the acetabular cup (along arrow C of FIG. 17, note that FIG. 17 is a perspective view from below so that an upper direction in FIG. 17 is actually downward on the page). When the portions of the liner 30 directly adjacent the annular seat 37 abut the locking ring 60, they abut the beveled edge 69. This beveled edge 69 allows for transfer of radial forces outward on the locking ring 60 as the liner 30 is further translated upward (arrow C of FIG. 17). The locking ring 60 is thus expanded radially to extend deeper into the annular groove 19 and widening the break 61 (arrow D of FIG. 17).

Also, during this expansion the slot 72 moves relative to the post 17 so that the inner end 74 of the slot 72 is adjacent the post 17. Thus, the captured end 70 of the locking ring 60 moves sufficiently away from the center of the acetabular cup 10 so that the liner 30 can pass entirely into the acetabular cup 10. When the annular seat 37 of the liner 30 achieves a plane coplanar with the annular groove 19, the locking ring 60 can snap back into the annular seat 37 and return to its undeformed position (FIG. 18). The liner 30 is thus securely held within the acetabular cup 10. The last linear motion of the liner 30 results in compression of the top cone 40 around the top bore 20, with position of the locking ring 60 within the seat 37 of the liner 30 occurring after deflection of the edge 46 of the top cone 40 or otherwise pressing the deforming seal to seal the top bore 20 of the acetabular cup 10.

If the liner 30 needs to be removed, such as if the surgeon is not satisfied with the positioning of the liner 30 or wishes to substitute the liner 30 with a different liner 30, or notices a defect in the liner 30, the liner 30 can be easily removed or repositioned as follows. The finger 84 of the free end 80 is grasped and moved away from the captured end 70 (along arrow E of FIG. 18). This causes the slot 72 to slide radially outwardly (along arrow F of FIG. 17) and to cause the break 61 to be widened (along arrow D of FIG. 17) such that the locking ring 60 extends radially deeper into the annular groove 19 and out of the annular seat 37 of the liner 30. The liner 30 can then be removed. A separate liner 30 can then be inserted following the steps identified above.

If the locking ring 60 is to be removed from the acetabular cup 10, the finger 84 of the free end 80 is grasped and moved toward the captured end 70. This causes the slot 72 to slide until the post 17 is adjacent the outer end 73 of the slot 72 and causes the locking ring 60 to achieve a lesser diameter by the shrinkage of the break 61 (along arrow B of FIG. 18). The locking ring 60 can then be removed.

This disclosure is provided to reveal a preferred embodiment of the invention and a best mode for practicing the invention. Having thus described the invention in this way, it should be apparent that various different modifications can be made to the preferred embodiment without departing from the scope and spirit of this invention disclosure. When structures are identified as a means to perform a function, the identification is intended to include all structures which can perform the function specified. When structures of this invention are identified as being coupled together, such language should be interpreted broadly to include the structures being coupled directly together or coupled together through intervening structures. Such coupling could be permanent or temporary and either in a rigid fashion or in a fashion which allows pivoting, sliding or other relative motion while still providing some form of attachment, unless specifically restricted.

What is claimed is:

1. A locking ring, liner and acetabular cup combination for an artificial hip joint, comprising in combination:
   an acetabular cup having an exterior surface adapted to abut a hipbone and be held securely to the hip bone;
   said acetabular cup having a generally concave interior surface;
   said acetabular cup having an annular groove facing inward from said generally concave interior surface;
   a liner having an outside surface adapted to mate within said generally concave interior surface of said acetabular cup;
   said liner having a generally concave inside surface adapted to pivotably support a head of an artificial hip joint coupled to an upper end of a femur;
   said liner having an annular seat facing outward from said outside surface of said liner;
   a locking ring having a top side spaced from a bottom side by a ring thickness that is less than a thickness of said groove of said acetabular cup and less than a thickness of said seat of said liner;
   an outer side spaced from an inner side by a ring width;
   said outer side having an undeformed diameter sufficient to extend at least partially into said groove of said acetabular cup;
   said inner side having an undeformed diameter sufficient to extend at least partially into said seat of said liner;
   said ring width less than a difference between a diameter of said groove of said acetabular cup and a diameter of said seat of said liner;
   a break in said ring, such that enlarging said break expands said outer side diameter and said inner side diameter, and narrowing said break reduces said outer diameter and said inner diameter;
   a captured end adjacent said break and a free end adjacent said break; and
   wherein said acetabular cup includes a pin affixed thereto adjacent said groove, and wherein a slot is provided at said captured end adapted to reside over said pin of said acetabular cup when said ring is located within said groove of said acetabular cup and within said seat of said liner, such that said ring holds said liner within said acetabular cup.

2. The combination of claim 1 wherein said slot is angled between an inner end and an outer end with said outer end extending further circumferentially along said ring than said inner end.

3. The combination of claim 2 wherein said captured end includes a nob extending beyond said outer side of said locking ring with said slot extending at least partially into said nob.

4. The combination of claim 2 wherein said free end includes a finger thereon, said finger extending beyond said outer side of said ring.

5. A locking ring, liner and acetabular cup combination for an artificial hip joint, comprising in combination:
   an acetabular cup having an exterior surface adapted to abut a hipbone and be held securely to the hip bone;
   said acetabular cup having a generally concave interior surface;
   said acetabular cup having an annular groove facing inward from said generally concave interior surface;
   a liner having an outside surface adapted to mate within said generally concave interior surface of said acetabular cup;
   said liner having a generally concave inside surface adapted to pivotably support a head of an artificial hip joint coupled to an upper end of a femur;
   said liner having an annular seat facing outward from said outside surface of said a locking ring having a top side spaced from a bottom side by a ring thickness that is less than a thickness of said groove of said acetabular cup and less than a thickness of said seat of said liner;
   an outer side spaced from an inner side by a ring width;
   said outer side having an undeformed diameter sufficient to extend at least partially into said groove of said acetabular cup;
   said inner side having an undeformed diameter sufficient to extend at least partially into said seat of said liner;
   said ring width less than a difference between a diameter of said groove of said acetabular cup and a diameter of said seat of said liner;
   a break in said ring such that enlarging said break expands said outer side diameter and said inner side diameter, and narrowing said break reduces said outer diameter and said inner diameter;
   a captured end adjacent said break and a free end adjacent said break; and
   wherein said combination includes a deforming seal interposed between said outside surface of said liner and said interior surface of said acetabular cup, said deforming seal located adjacent a top bore extending between said interior surface of said acetabular cup and said exterior surface of said acetabular cup, said deforming seal being deflected to said outside surface of said liner when said ring is located within both said groove of said acetabular cup and said seat of said liner.

6. The combination of claim 5 wherein said deforming seal is attached to said outside surface of said liner.

7. The combination of claim 6 wherein said deforming seal includes a circular edge sized to abut said interior surface of said acetabular cup surrounding said top bore.

8. The combination of claim 7 wherein said circular edge of said deformable seal defines a largest diameter edge of a cone formed of a material similar to a material from which other portions of said liner are formed and with sufficient thickness between an outer conical surface and an inner conical surface of said cone to allow said edge of said cone to be deflected toward said outside surface of said liner, when said locking ring resides within said groove of said acetabular cup and said seat of said liner with said edge of said cone abutting said interior surface of said acetabular cup surrounding said top bore.

* * * * *